United States Patent [19]
Richman

[11] Patent Number: 5,972,190
[45] Date of Patent: Oct. 26, 1999

[54] CONTINUOUS FLOW ELECTROPHORESIS APPARATUS

[75] Inventor: David W. Richman, Huntington Beach, Calif.

[73] Assignee: McDonnell Douglas Corporation, Huntington Beach, Calif.

[21] Appl. No.: 08/752,669

[22] Filed: Nov. 19, 1996

[51] Int. Cl.$^6$ ................................................. G01N 27/26
[52] U.S. Cl. ........................................................ 204/600
[58] Field of Search ................................... 204/450, 600

[56] References Cited

U.S. PATENT DOCUMENTS

| | | | |
|---|---|---|---|
| 3,616,453 | 10/1971 | Phillpot | 204/647 |
| 4,061,560 | 12/1977 | Hannig et al. | 204/600 |
| 4,309,268 | 1/1982 | Richman | 204/600 |
| 4,310,408 | 1/1982 | Rose et al. | 204/600 |
| 4,383,042 | 5/1983 | Coggins | 436/5 |
| 4,383,905 | 5/1983 | Richman | 204/518 |
| 4,394,246 | 7/1983 | Richman et al. | 204/600 |
| 4,465,582 | 8/1984 | Richman | 204/600 |
| 5,071,536 | 12/1991 | Ivory | 204/549 |
| 5,104,505 | 4/1992 | Tarnopolsky | 204/459 |
| 5,180,480 | 1/1993 | Manz | 204/644 |
| 5,298,143 | 3/1994 | Ivory et al. | 204/543 |
| 5,439,571 | 8/1995 | Sammons et al. | 204/549 |
| 5,454,472 | 10/1995 | Benecke et al. | 209/127.1 |

FOREIGN PATENT DOCUMENTS

1354093A1  1/1986  U.S.S.R. .

OTHER PUBLICATIONS

Derwent abstract of Kuznetsov (SU 1354093 A1), Jan. 1986.

*Primary Examiner*—Elizabeth McKane
*Assistant Examiner*—Alex Noguerola
*Attorney, Agent, or Firm*—Alston & Bird LLP

[57] ABSTRACT

An electrophoresis chamber having the separation capability of a thicker chamber by the addition of a number of ports along the length of the chamber that can act as inlets or outlets. The device introduces cross flow by either a plurality of input and output ports along opposite walls of the chamber or by a tapered chamber having a plurality of output ports. Since the mobility of the particles is lateral to the direction of flow and the cross flow velocity is opposite in direction and greater than the maximum electrophoretic velocity of the particles being separated such particles are carried to the wall of a narrow linear chamber and will pass through ports provided in the wall spaced at strategic distances along the wall separation is achieved. In addition, because the sample and the outlet electrode surface are of like sign there is no deposition of the sample on the electrode surface.

25 Claims, 10 Drawing Sheets

CONTINUOUS FLOW ELECTROPHORESIS APPARATUS

BACKGROUND OF INVENTION

1. Field of Invention

The field of this invention relates to methods and apparatus for continuous electrophoresis, that is, the separating of mixtures of microscopic charged particles in samples. More specifically, this method of continuously separating mixtures of microscopic charged particles relates to apparatus having distributive output ports for the collection of such particles in an electrical field.

2. Related Art

There are numerous methods of continuously separating mixtures of particles in electrophoresis devices. These are typified by U.S. Pat. No. 3,412,008 to STRICKLER, U.S. Pat. No. 4,061,560 to HANNIG, and U.S. Pat. No. 4,310,418 to ROSE/RICHMAN. The free flow electrophoretic process described in such patents is the result of a combination of several phenomena. The process generally utilizes a continuous laminar flow of a carrier fluid or buffer 5 through a chamber with multiple outlets as shown in FIGS. 1, 2, and 3. The sample stream 1 containing a protein or other cell particles is input into this flow and an electrical field applied to the flow in the direction generally perpendicular to the flow. The basis for separation is the resulting electrophoresis of the samples or the motion of charged particles in an electrical field. This motion is the result of the force, on the particles, which is proportional to the charge and the electrical field strength. Under the influence of this force, the particles are accelerated in a direction lateral to flow direction and approach a terminal velocity, which is the velocity reached when the force of the viscous drag on the particles and the force of the electrical field reach equilibrium. The basis for separation is that different particles generally have different lateral terminal velocities and, therefore, leave the chamber through a different exit port strategically placed for collection, thereby providing a separation device. A typical wide chamber as shown in FIG. 1 provides sufficient width to accommodate the range of mobility predicted for the sample 1. The phenomena is quantified by a characteristic known as particle mobility which is the velocity component in the direction of the electric field divided by the electrical field strength. In other prior related art, the electric field is applied across a thickness dimension of an electrophoresis chamber as shown in FIGS. 2 and 3 and a sample 1 to be separated is inserted in the laminar flow layer in the chamber. Such a method was proposed to NASA in the mid-1970s by A. STRICKLER of Beckman Instruments. This method was found to have two major faults. First, the heating of the buffer due to the electrical field and heat removal from the walls of the chamber caused convection cells which disrupted the flow at the output end of the chamber. Second, attempts to suppress the convection flow by limiting the chamber thickness resulted in very thin sample and outlet fraction layers which mixed by concentration driven diffusion thereby spoiling the separation. Electrophoresis chambers of this type have been addressed by PHILPOT in U.S. Pat. No. 3,616,453 where flow is layered between a fixed inner cylindrical wall and a rotating outer cylindrical wall causing stabilizing monotonic increases in angular momentum from the inner cylinder to the outer cylinder. The rotating cylindrical approach, while addressing these problems, results in a significant increase in mechanical complexity and potential reliability problems. The PHILPOT device as configured has 30 output fractions limiting its resolution potential. However, a relatively large sample cross-section gives it a large throughput potential.

BRIEF DESCRIPTION OF THE INVENTION

One embodiment of the instant device comprises a thin linear or planar chamber with the separation capability of a thicker chamber by the addition of a number of ports along the length of the chamber that can act as inlets or outlets. The principle embodied in the device is that since the mobility of the particles is lateral to the direction of flow and the cross flow velocity is opposite in direction and greater than the maximum electrophoretic velocity of the particles being separated, such particles are carried to the wall of a narrow linear chamber and will pass through ports provided in the wall spaced at strategic distances along the wall and separation is achieved.

In this invention, a sample whose component of interest has a positive electrophoretic mobility is input at some arbitrary distance away from the cathode toward the anode. Since most particles of interest are negatively charged, they tend to separate by attraction to the anode at different electrophoretic mobilities. However, the greater cross flow toward the negative electrode overcomes the positive electrophoretic motion and velocity and carries the separated sample component toward the cathode and out of the chamber through one of the ports with the flow at the cathode where it is collected.

Because the sample and the cathode surface are of like sign there is no deposition of the sample on the electrode surface.

Another embodiment provides a chamber of the instant invention which is constructed in a generally cylindrical form. This chamber also has multiple buffer inlets so that the sample can be input at the desired location between anode and cathode, as governed by the relative flows through the inlets. The inlet section is followed by electrode segments having outlets and inlets spaced along a cylindrical column surrounding the anode. Equally spaced inlets and outlets of equal flow are used. However, the basic principles involved also apply to arbitrarily spaced inlets and outlets with arbitrary flow rates and the design is equally applicable to a planar and cylindrical chambers. For a planar chamber, plenums would be used to equalize the flow along the inlet and outlet slots along the side of the chamber. For a cylindrical chamber the buffer and sample inlet plenums may be replaced by porting these flows at the cylindrical centerline.

The walls of the electrode segments can be constructed in the usual way, as either ion permeable or ion exchange membranes, with the electrodes having separate rinse flows to carry away the gasses liberated by electrolysis of the carrier buffer. In the preferred embodiment, they are constructed as part of the surfaces of the electrodes themselves. The electrode surface is constructed of non-reactive material such as a noble metal (gold, platinum, etc) or graphite. Construction of electrodes without membranes, however, reduces the complexity of the apparatus greatly as well as eliminating the undesirable pH changes that occur in the vicinity of membranes, especially where the membranes are in close proximity to the separated sample. This construction only requires that the amount of gas liberated by electrolysis be absorbed by the degassed buffer fluid. This can be accomplished by limiting the applied voltage and resulting current.

While the above identified embodiment includes a relatively uniform chamber having inlets and outlets, in another embodiment, the outlets for the separated fractions are distributed uniformly along the wall of the device which forms a uniformly tapered cross section chamber. This results in constant centerline velocity and eliminates the need for multiple buffer inlets. Because the centerline velocity is high relative to any convective velocities caused by Joule heating of the buffer and also because the chamber thickness is decreasing toward the outlet thereby increasing viscous damping of convective flows, the chamber is more resistant to convective disturbance than a chamber of rectangular cross section.

In a tapered chamber, a high mobility sample inserted at the centerline proceeds along the centerline and exits at the apex of the tapered section. Components with lower mobilities exit through the outlets in the wall of the chamber before reaching the apex.

By tapering the cross section of the separation chamber and distributing the outlets from the chamber along the lateral wall, the distributed outlet method can be greatly simplified and improved in terms of resistance to gravity induced convective disturbances in the flow. Because of the large throughput available by the configuration of this device, it is particularly useful for the separation of enzymes produced by genetically engineered cells or bacteria, because of the need for significant amounts required for a therapeutic dose.

The specific structure of the device includes a number of stacked segments which are separated by insulating gaskets and are electrically connected through a resistor network. The resistor network progressively reduces the voltage difference across the annular space so that it is proportional to its thickness, thereby applying a constant electrical field strength, as measured in volts/cm across the tapered chamber. The total current is dependent on buffer conductivity and therefore, the resistance values required are similarly dependent. Differences in buffer conductivity can be accommodated by the use of variable resistance potentiometers in the resistor network to adjust the resistances to account for differences in such conductivity and ensure constant electric field strength.

To effect separation, the sample is inserted close to the cathode. To accomplish this, most of the buffer flow enters through the anode buffer inlet and the sample is inserted around its periphery. The remaining (cathode) buffer flow is added around the periphery of the chamber. If the distribution is not sufficiently uniform, additional cathode inlets can be used along with an external distribution manifold to attain the desired degree of uniformity.

The anode and the cathode, are of course, made of conductive materials, however, the inlet is constructed of non-conductive material to confine the electrophoresis process to the tapered annular chamber. Materials for the tapered anode and the cathode segments should be corrosion resistant. Possible candidate materials include graphite or titanium or less corrosion resistant metals plated with noble metals such as gold or platinum, for example. The inlet section should be constructed of non-conductive material like non-conductive composites or engineering plastics.

Buffer inlet tubes can be attached through the use of standard fittings. Sample inlet and outlet tubes are significantly smaller and use either miniature fittings or are glued in place. Outlet lines must be of sufficient length to meter the flows to approximately equal amounts and to reach a terminus in a manifold at a common geometric height (pressure head) for collection of separated samples.

as it relates to the radial length of the slot.

Figure 16:
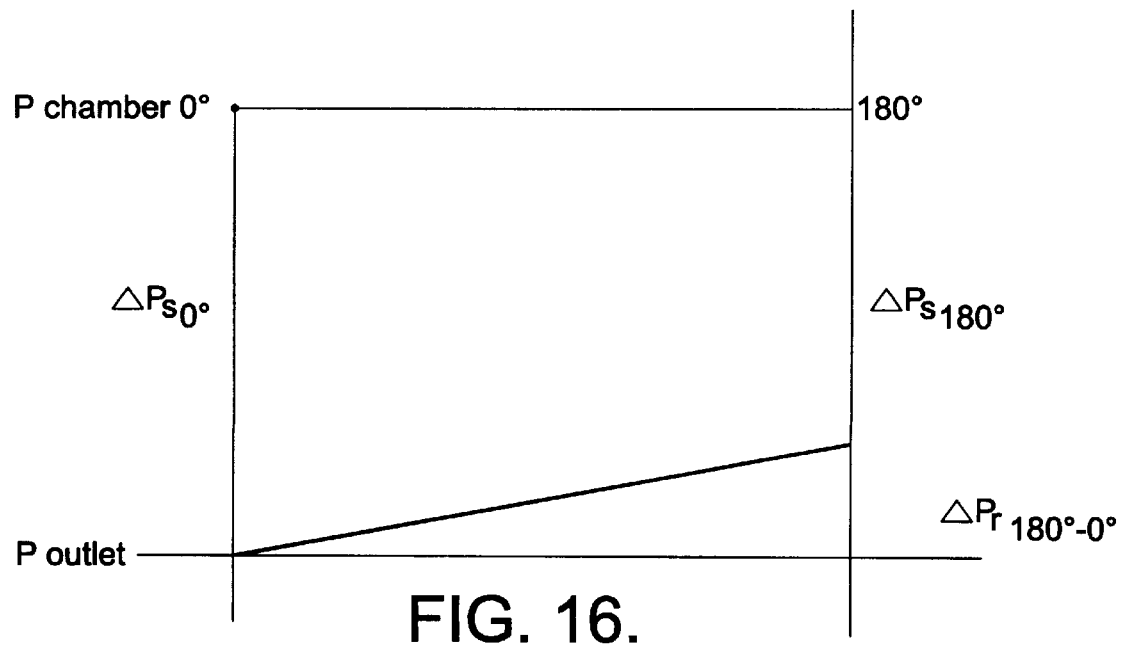

FIG. 16 illustrates pressure equalization wherein the change in pressure due to the alot is equalized by the change in pressure of the recess.

SPECIFIC EMBODIMENT

Figure 1:
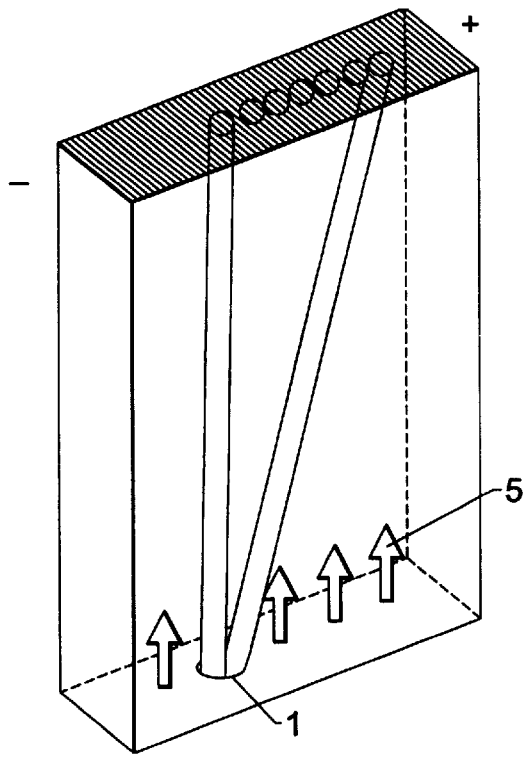
FIG. 1 is an electrophoresis chamber with distribution of particles of interest across the width of the chamber.
Figure 2:
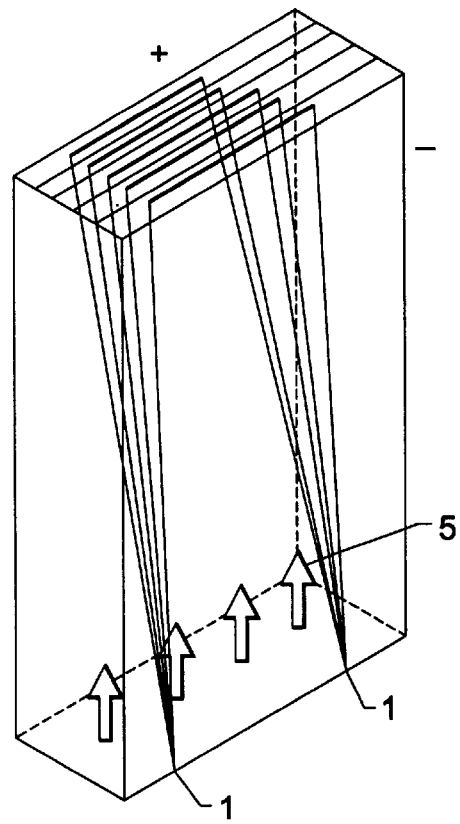
FIGS. 2 and 3 are illustrations of electrophoresis chambers with separation across the thickness of the chamber.
Figure 3:
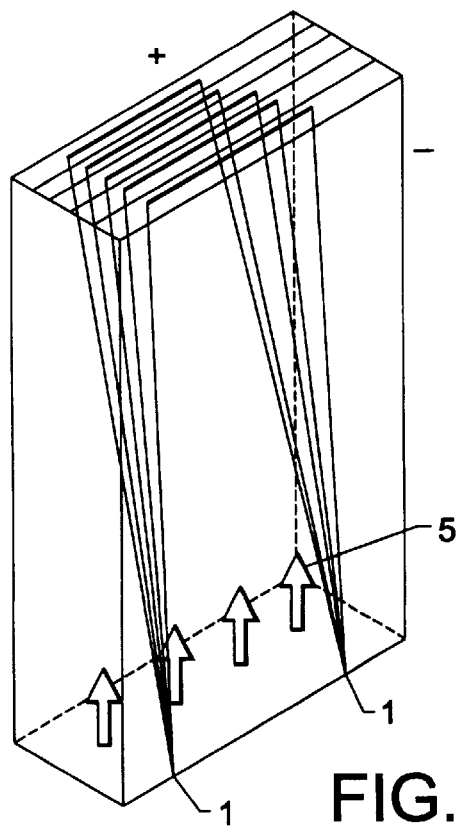
Figure 4:
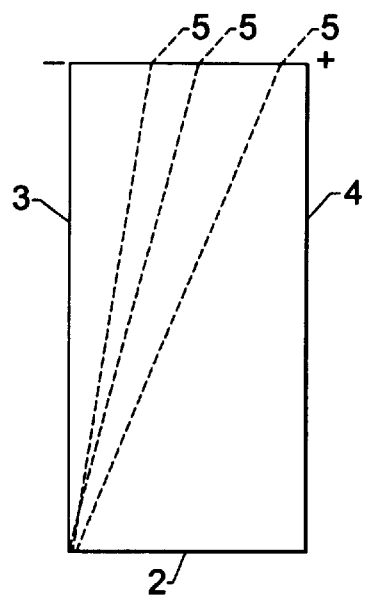
FIG. 4 is a diagramical representation of electrophoresis effect on introduced samples spreading across the chamber.
Figure 5:
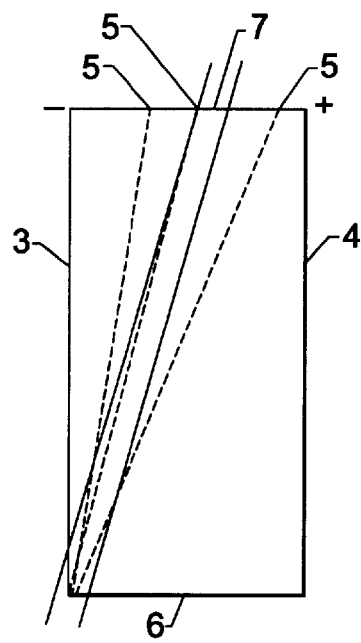
FIG. 5 shows the concept of a narrow chamber intercepting the spread of samples for isolated regions.
Figure 6:
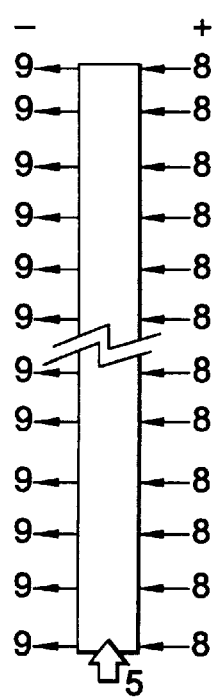
FIG. 6 shows a plurality of inputs and outputs in a electrophoresis chamber.

A thin chamber as in the STRICKLER device or a thin annulus as in the PHILPOT device may be used which allows the thin chamber to have the separation capability of a thicker chamber or annulus by the addition of a number of ports along the length of the chamber that can act as inlets or outlets. The principle embodied in the device is illustrated in FIGS. 4 and 5. In FIG. 4, a fan shaped separation pattern with separation elements in sheets or layers in a wide chamber 2 is shown. The left edge 3 of this pattern corresponds to minimum mobility, the right edge 4 to maximum mobility, and dotted lines to the mobility range of some components of interest 5. In FIG. 5, the walls of an arbitrary thinner chamber or annulus 7 are superimposed on the flow so that the mobility of the components of interest 5 are such that they are carried to the walls of the arbitrary chamber 7. It is clear from FIG. 5 that the arbitrary walls superimposed on the flow cause the flow to have a longitudinal as well as cross flow component in the chamber 7. To eliminate the large chamber in favor of the smaller chamber requires that the cross flow be introduced. This requires not only ports 9 in the walls as shown in FIG. 6 that can act as outlets 9 for the chamber flow but also a series of buffer inlets 8 provided for uniform buffer flow. It should be noted that FIGS. 4 and 5 are intended only to illustrate the principles involved in using a thinner chamber. In reality, viscous shear results in a generally parabolic velocity distribution between the walls causing the paths of the components to be curved as opposed to straight lines as illustrated.

Figure 7A:
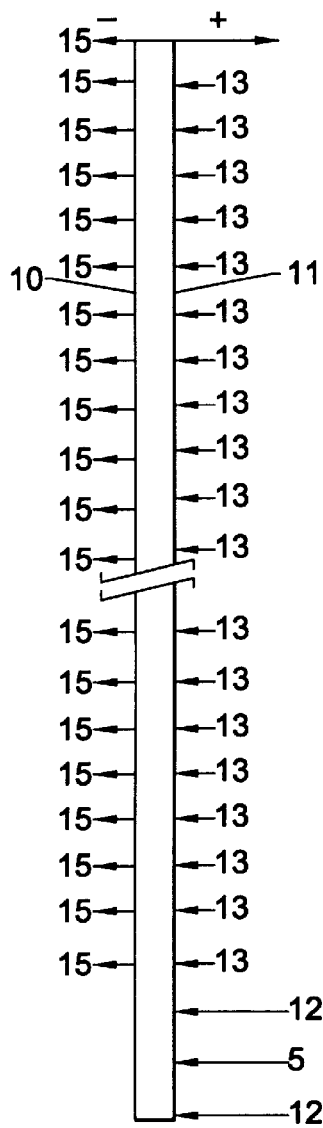
FIGS. 7A, 7B & 7C show the invention having a plurality of input and output plenums, in a uniform width chamber.

The path of a sample component 5 of negative charge and therefore positive electrophoretic mobility in a chamber with a negative cross flow velocity greater than the electrophoretic velocity is illustrated in FIG. 7A. In the preferred embodiment of this invention a sample 5 whose component of interest has a positive electrophoretic mobility is input at some arbitrary distance away from the cathode 10 toward the anode 11. The greater negative cross flow velocity then carries the sample component toward the cathode and out of the chamber with the flow exiting at the cathode where it is collected. In this case, because the sample and the cathode surface are of like sign there is no deposition of the sample on the electrode surface.

Figure 7B:
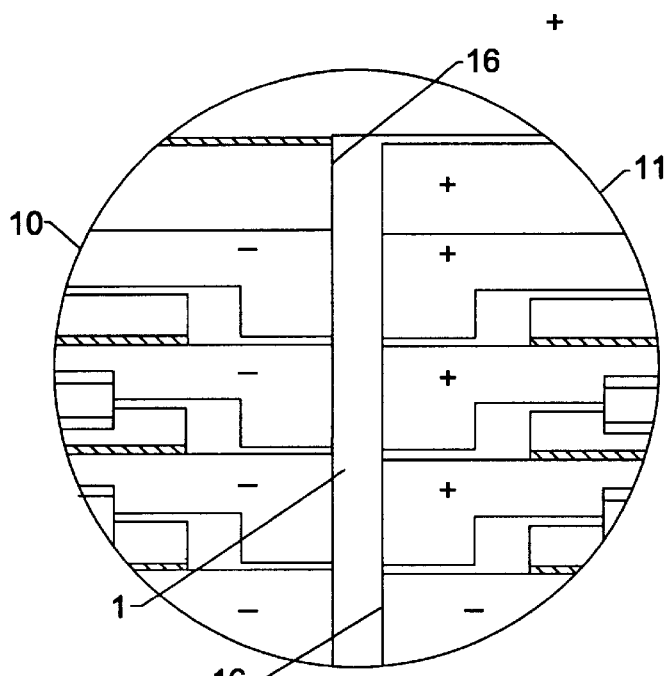
Figure 7C:
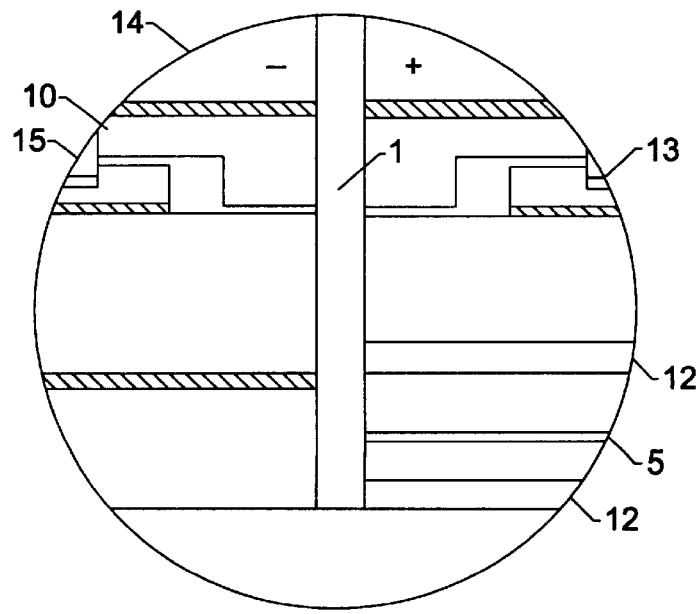

The chamber cross section embodying these principles is shown in FIG. 7B and 7C. This chamber 1 has multiple buffer inlets 12 so that the sample 5 can be input at the desired location between anode and cathode, as governed by the relative flows through the inlets plenum tubes 12. The inlet 12 section is followed by electrode segments 14 and buffer inlet plenum tubes 13 and outlet plenum tubes 15 spaced along the column. While equally spaced inlets 13 and outlets 15 of equal flow are shown in FIG. 7A, the basic principles involved also apply to arbitrarily spaced inlets and outlets with arbitrary flow rates. The cross section shown in FIG. 7A is applicable to either a planar chamber or an annular chamber. For a planar chamber the inlets and outlets are spaced along the side of the chamber to equalize the flow. For a cylindrical chamber inlets 13 and outlets 15 are similarly spaced. However, the buffer inlet 12 and sample inlet 5 could be replaced by porting these inlets 12 and 5 flows at the cylindrical centerline.

The walls 16 of electrode segments could be constructed in the usual way as either ion permeable or ion exchange membranes (not shown), with the electrodes 14 having separate rinse flows to carry away the gasses liberated by electrolysis of the carrier buffer.

The walls 16 as shown are constructed as part of the surfaces of the electrodes 14 themselves. The electrode 14 surface is constructed of non-reactive material such as the noble metals (gold, platinum, etc) or graphite for example or lesser resistant metals plated with such non-reactive metals. Membraneless construction of the electrodes 14 reduces the complexity of the apparatus greatly as well as eliminating the undesirable pH changes that occur in the vicinity of membranes, especially where the membranes are in close proximity to the separated sample 5.

The simplified construction of the instant invention as disclosed herein provides a uniform cross flow though a series of controlled inlet flows.

Figure 8A:
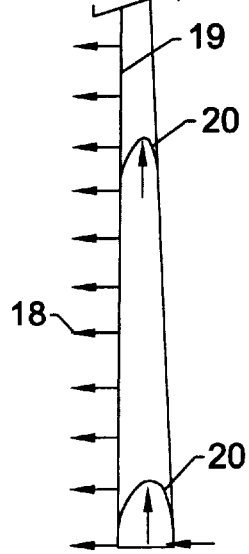
FIGS. 8A, 8B and 8C show the electrophoresis chamber with a tapered configuration.
Figure 8B:
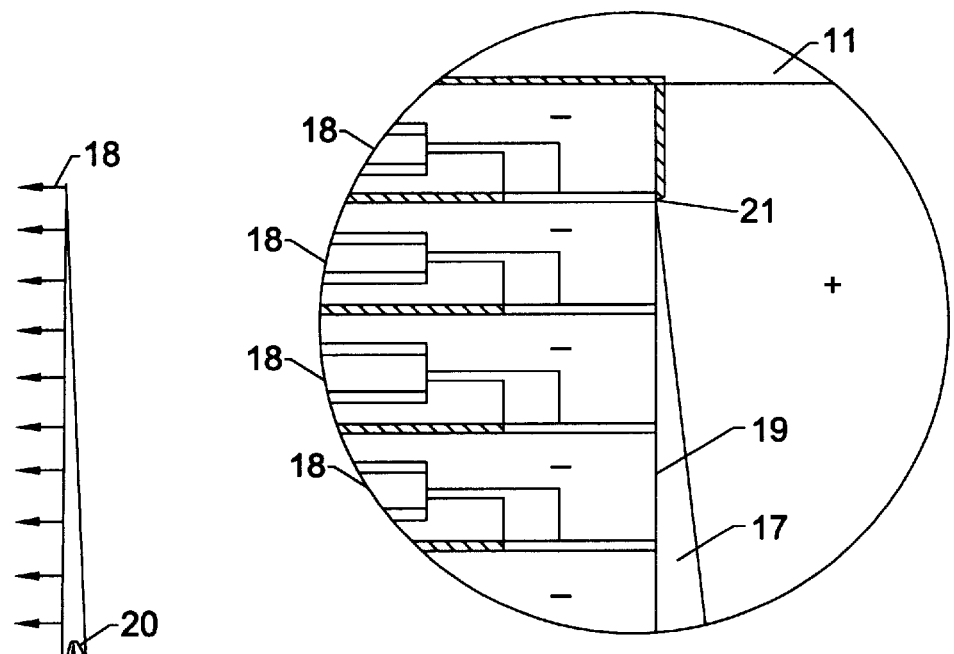
Figure 8C:
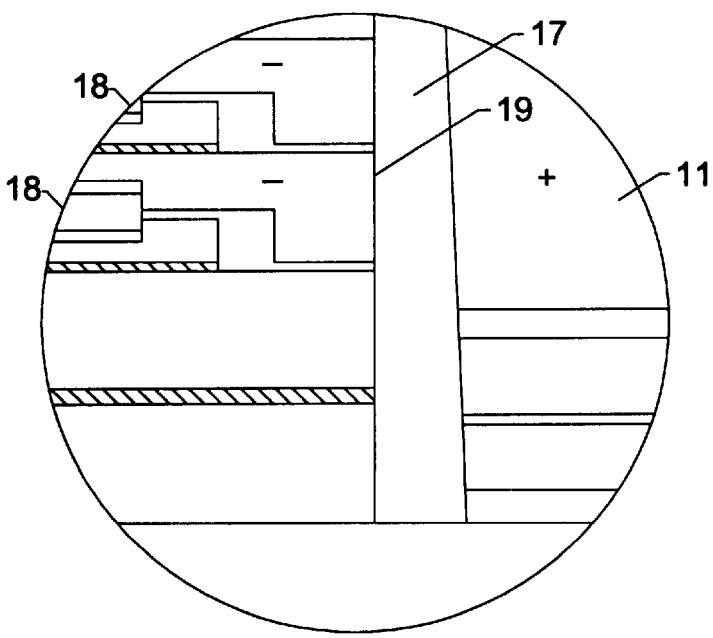

Another embodiment of this invention is the use of a tapered chamber as shown in FIG. 8. This tapered design eliminates the need for the controlled flow 50 at the end of the chamber as shown in FIG. 7A. That is, all of the remaining buffer and remaining samples having high mobility exit through the last outlet port. The tapered chamber eliminates the need for individual cross flow inlet ports. It is clear that the sum of the outlet flows of the separated fractions and buffer along the wall of the tapered chamber 17 must, by conservation of mass, equal the inlet flow to the chamber. If the outlets 18 for the separated fractions are distributed uniformly along the wall, then the uniformly tapered cross section of the tapered chamber 17, results in approximately parabolic velocity profiles with a constant centerline velocity 20. That is, the angle of the tapered chamber 17 must be such as to provide a constant centerline velocity relative to the wall 19 of the chamber considering the amount of mass extracted from the chamber 17 as the flow proceeds along the length of the chamber wall 19.

In addition, because the centerline velocity 20 through the chamber 17 is high relative to any convective velocities caused by Joule heating of the buffer and also because the chamber 17 thickness is decreasing toward the final outlet 18 while the viscous damping of convective flows is increasing, the chamber is resistant to convective disturbance.

If we approximate constant outflow along the wall by having many outlets then, because of the dominance of viscous shear within the thin cross section, the longitudinal velocity profile is approximately parabolic the following follows:

$$V_x = V_{CL}\left(1 - \left(\frac{yl}{bx}\right)^2\right) \quad (1)$$

Where
$V_x$=velocity in the −x direction, cm/sec
$V_{CL}$=centerline velocity, cm/sec
y=lateral distance from centerline, cm
b=chamber half thickness at the inlet, cm
x=distance along the centerline from the outlet, cm
l=chamber length, cm and for small ratios of half thickness to length and fully developed laminar flow, we have setting outlet flow equal to inlet flow:

$$lV_{out} = \frac{2}{3}V_{CL}2b \quad (2)$$

or $$V_{out} = \frac{4}{3}\frac{V_{CL}b}{l}$$

where Vout=outlet flow velocity, cm/sec and because the action of viscous shear maintains the parabolic velocity profile the added crossflow starting at the solid +y wall of the chamber integrated in the −y direction is proportional to the local x velocity, therefore:

$$V_{CF} = \frac{-2}{3}\frac{V_{CL}b}{l} + \int_0^y \frac{V_{CL}}{l}\left(1 - \left(\frac{yl}{bx}\right)^2\right)dy^2 \quad (3)$$

or $$V_{CF} = \frac{-2}{3}\frac{V_{CL}b}{l} + \frac{V_{CL}}{lx}\left(y - \frac{y^3 l^2}{3b^2 x^2}\right) \quad (4)$$

where $V_{CF}$=cross flow velocity, cm/sec which is perpendicular to the local velocity component in the direction toward the apex of the tapered cross section.

And the velocity in the y direction is therefore:

$$V_y = V_{CF} + \mu_E E - \frac{y}{x}V_x \quad (5)$$

where $V_y$=total velocity in the y direction, cm/sec $$\frac{-yV_x}{x} =$$

the component of the velocity toward the apex in the y direction

Examining equation (5) we see that if the sample 5 is inserted at the centerline (y=0) and if $V_{CF}=-\mu_E E$, then $V_y=0$ and the sample proceeds along the centerline and exits at the apex 21 of the tapered section. Components with lower mobilities exit at various locations through the outlets in the −y wall of the chamber 17. If for example, the maximum mobility is $3\times10^{-4}$ cm²/volt-sec and:

$l=100$ cm $b=0.15$ cm $V_{CL}=1.0$ cm/sec then $\mu_E=3.333$ volt/cm and integrating stepwise from the inlet we have for various mobilities that:

| $\mu$ cm²/volt-sec | $\tau$ outlet sec | d outlet cm |
|---|---|---|
| $3.0 \times 10^{-4}$ | 100.00 | 100.00 |
| $2.5 \times 10^{-4}$ | 101.37 | 99.03 |
| $2.0 \times 10^{-4}$ | 103.03 | 94.81 |
| $1.0 \times 10^{-4}$ | 94.40 | 78.76 |
| 0. | 80.80 | 65.03 |

Therefore, we see that a relatively wide mobility spectrum is spread over about one-third of the chamber length. As in the case of the rectangular chamber, this can be improved by inserting the sample 5 closer to the outlet wall 17. For example, insertion midway between the centerline and the outlet wall:

| $\mu$ cm²/volt-sec | $\tau$ outlet sec | d outlet cm |
|---|---|---|
| $3.0 \times 10^{-4}$ | 134.47 | 99.99 |
| $2.5 \times 10^{-4}$ | 143.01 | 84.10 |
| $2.0 \times 10^{-4}$ | 110.69 | 62.12 |
| $1.0 \times 10^{-4}$ | 79.27 | 39.87 |
| 0. | 58.52 | 29.90 |

Here we see that components differing by mobility unit from the maximum are separated by about 38% of chamber length, improving resolution. We also see that the residence time from the inlet to the outlet is greater than the 100 seconds along the centerline. Taking this one step further, for injection at two-thirds of the distance from the centerline to the outlet wall we have:

| $\mu$ cm²/volt-sec | $\tau$ outlet sec | d outlet cm |
|---|---|---|
| $3.0 \times 10^{-4}$ | 184.23 | 99.81 |
| $2.5 \times 10^{-4}$ | 161.03 | 59.88 |
| $2.0 \times 10^{-4}$ | 106.34 | 38.20 |
| $1.0 \times 10^{-4}$ | 61.87 | 22.69 |
| 0. | 43.72 | 15.80 |

In this case the resolution is approximately doubled relative to the previous case for mobilities near the maximum.

From the foregoing it is apparent that by tapering the cross section of the separation chamber 17 and distributing the outlets 18 from the chamber 17 along one of the lateral walls 19, that the implementation of the distributed outlet is greatly simplified and improved in terms of resistance to gravity induced convective disturbances in the flow. This results in a large throughput and is particularly useful for the separation of enzymes produced by genetically engineered cells or bacteria, because of the volume required for therapeutic dosage.

Figure 9:
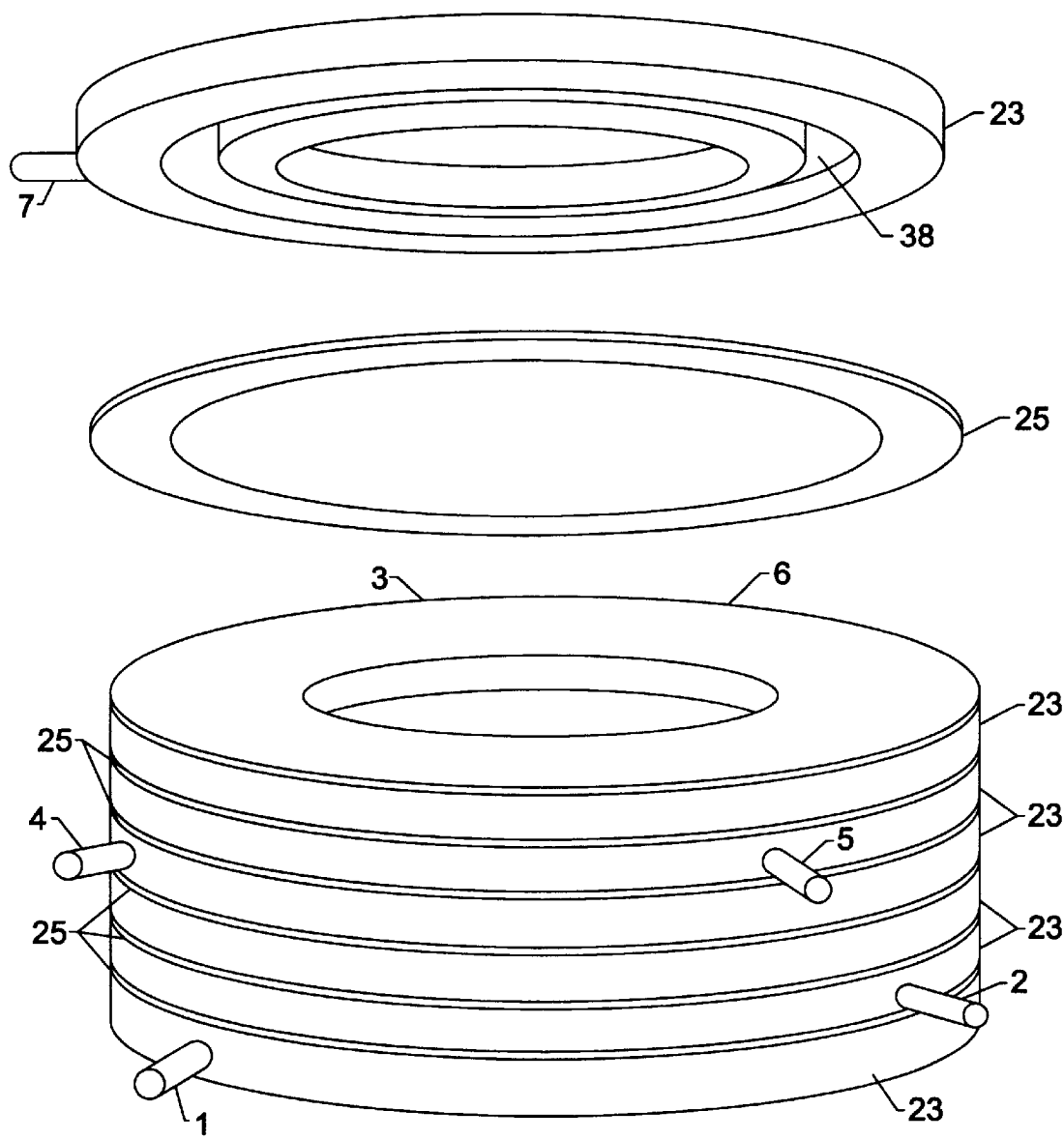
FIG. 9 shows the annular cathode output stacks which surround the anode in exploded form.
Figure 10:
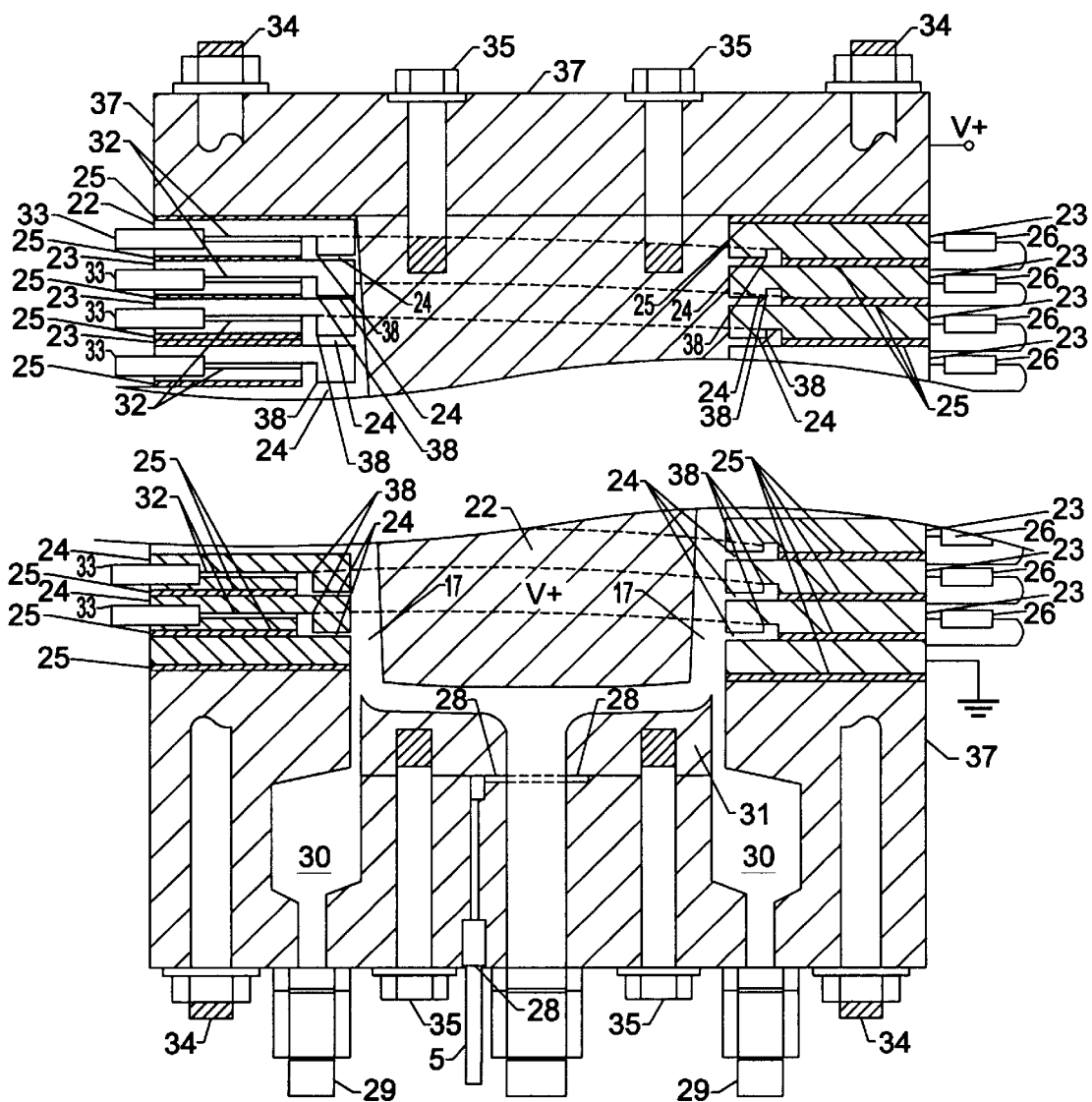
FIG. 10 is a cross-sectional view of the electrophoresis chamber showing the stacked configuration and the central position of the anode.

The specific construction detail of a the tapered annular electrophoresis chamber 17 as disclosed herein is illustrated in FIGS. 9 and 10, The outside diameter of the annulus 22 shown in FIG. 10 is about 10 cm and the length of the annulus 22 is about 100 cm. The outside of the annulus 22 is the cathode 23 and in this embodiment is composed of 100 conductive outlet annular segments 24.

Figure 12:
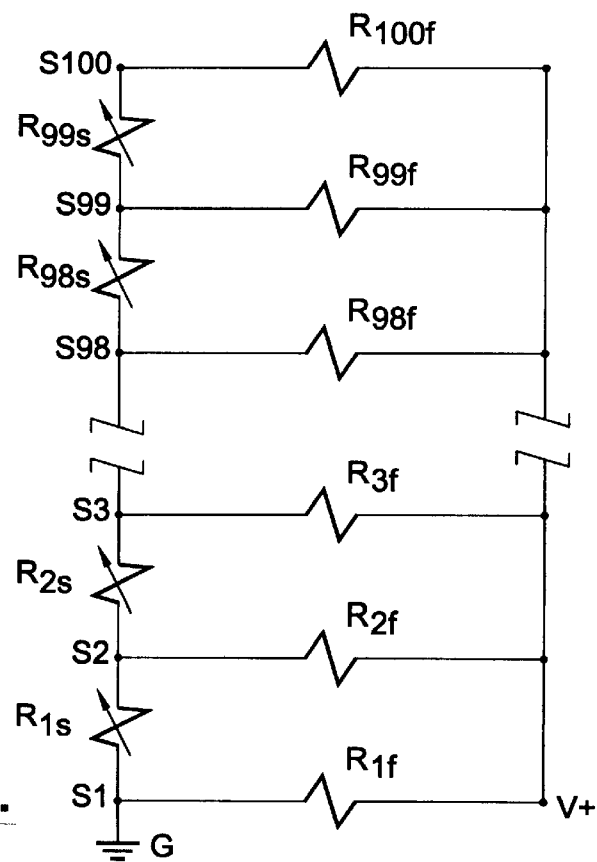
FIG. 12 shows the resistance structure incorporating the internal fluid resistance and the external resistance.

The annular segments 24 are separated by insulating gaskets 25 by a sufficient amount to capture the target sample 5 carried by the buffer. This distance is less than a millimeter in the specific structure herein described and the electrodes are electrically connected by a resistor network 26 to reduce the voltage difference across the annular space 17 in proportion to its thickness and achieve a constant electrical field strength, as measured in volts/cm across the gap. For example, since there are 100 segments 24, each segment must pass 1% of the total current, the resistance of the first resistor between the first (cathode) segment and the second segment should be such that it passes 99% of the current at 1% of the applied voltage. It should be noted that the fluid in the chamber is essentially a parallel resistance path to the external resistance thus the resistance network is a series parallel network as illustrated in FIG. 12. The resistance of the second resistor should be such that it passes 98% of the current at 1% of the applied voltage and so forth, until the final resistor passes 1% of the current at 1% of the applied voltage. Since the total current is dependent on buffer conductivity, the resistance values required are similarly dependent. Adjustment for differences in buffer conductivity can be accommodated by the use of variable resistance potentiometers as part of the resistance network.

As noted above the purpose of the resistor network is to progressively reduce the voltage difference across the annular space so that it is proportional to its thickness, thereby applying a constant field strength. To effect this, resistances are placed in series between the cathode segments, so that the external resistances in combination with the resistance of the buffer fluid in the annular space form a series—parallel network. The network, going from the cathode ground is as shown in FIG. 12. The gap being considered is tapered, except that the minimum gap should be approximately equal to the slot thickness between the segments 24.

Referring to FIG. 12 the resistances are as follows:

$$R_{99s} = \frac{.01V}{.01I} - \frac{t_{min}}{C\pi Dl} \qquad R_{100f} \cong \frac{t_{min}}{C\pi Dl} = R_{min}$$

$$R_{98s} = \frac{.01V}{.02I} \qquad R_{99f} \cong \frac{.015t}{C\pi Dl}$$

$$R_{98f} \cong \frac{.025t}{C\pi Dl}$$

$$R_{3f} \cong \frac{.975t}{C\pi Dl}$$

$$R_{2s} = \frac{.01V}{.98I} \qquad R_{2f} \cong \frac{.985t}{C\pi Dl}$$

$$R_{1s} = \frac{.01V}{.99I} \qquad R_{1f} \cong \frac{.995t}{C\pi Dl}$$

Where:
l=segment length
t=annular gap
C=buffer conductivity
D=average diameter

V+=Common Anode Voltage
G=Ground
$R_{ns}$=External Segment resistance (1<n<99)
$R_{mf}$=Fluid resistance (1<m<100)

At constant field strength the buffer in the gap adjacent to each segment will carry an equal share of the total current. Therefore, $R_{1s}$ must carry 99% of the total current at 1/100 of the applied common anode voltage of $$R_{1s} = \frac{.01V}{.99I}$$

and, $R_{2s}$, must carry 98% of the total current at 1/100 of the applied common voltage $$R_{2s} = \frac{.01V}{.98I}$$

This generalization works until $R_{99}$ where the minimum gap requires that $$R_{99s} + R_{min} = \frac{.01V}{.01I}$$

or $$R_{99s} = \frac{.01V}{.01I} - \frac{t_{min}}{C\pi Dl}$$

To accommodate buffer fluids of varying resistances the external resistances should be variable potentiometers, as shown. In production versions of the device these could be servo driven to values calculated by a process computer.

Where the values for the various resistances above are not generally available and an alternative resistance structure may be used to accomplish the same voltage requirements. For example, each compensating resistance may be dropped to ground directly from each segment.

Figure 13:
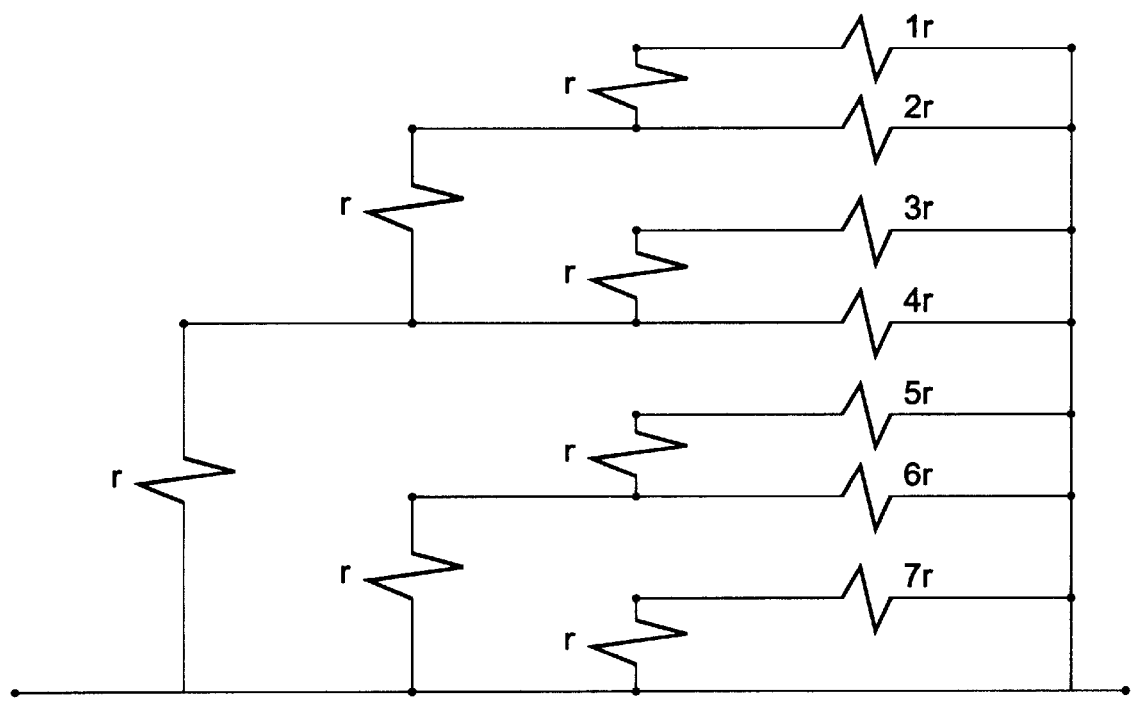
FIG. 13 shows an alternative resistance tree for an 8 branch tree.
Figure 14:
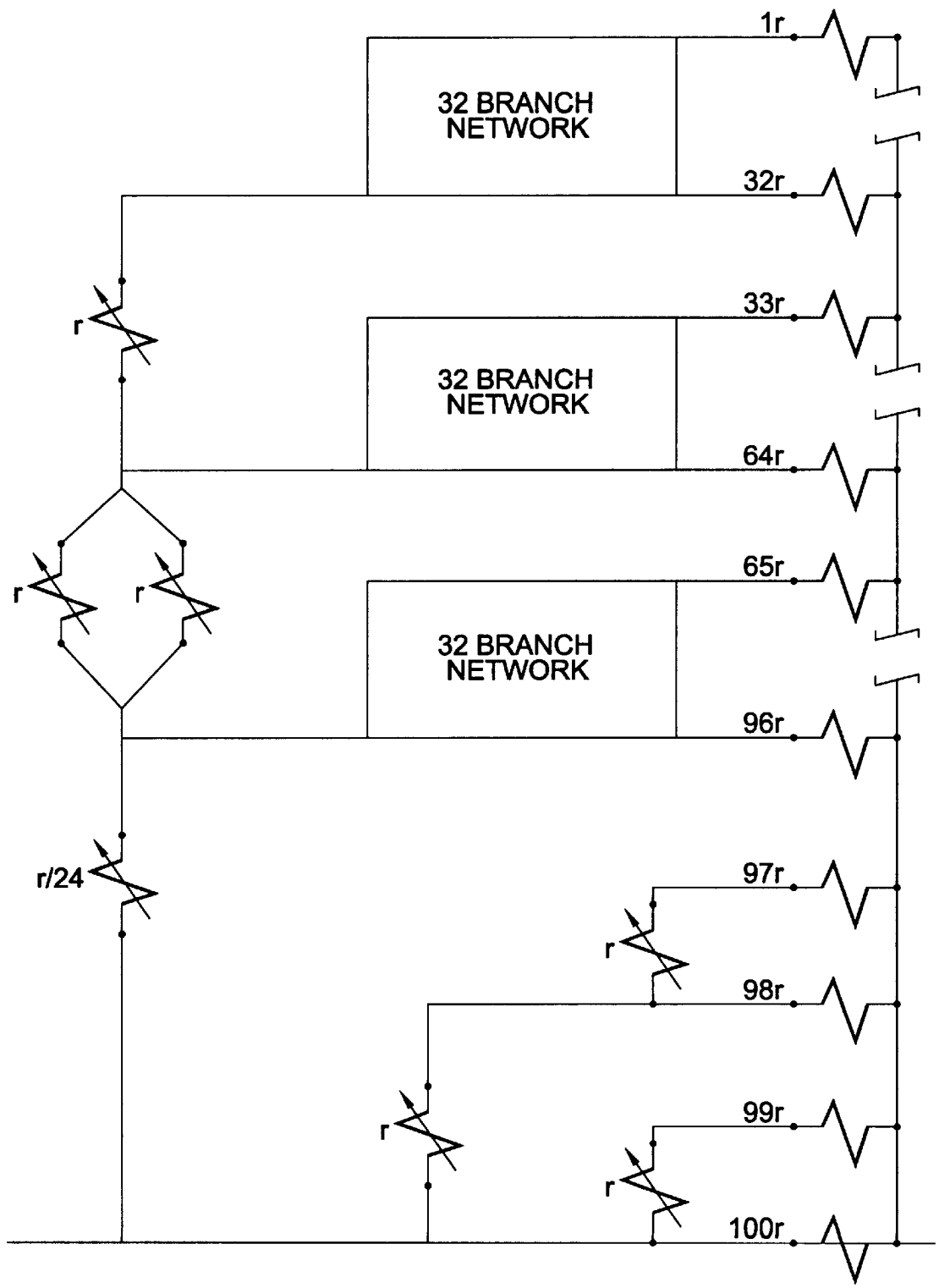
FIG. 14 shows the resistance tree for 100 branches.

More ideally, a resistance tree approach can be implemented which incorporates a common resistance r as shown in FIG. 13 for an eight branch network. In such a case, each resistance "r" (which is a potentiometer) may be ganged on a single shaft so that uniform adjustment of all resistances at once may be achieved. A close examination of the eight branch tree shown in FIG. 13 shows that the total resistance of the tree including the resistance of the fluid resolves to "r". This tree may be extended into a resistance tree of 32 branches. Three 32 branch trees may be combined in parallel as shown in FIG. 14 with 4 additional branches for a total of 100 branches as used in the preferred embodiment. The resistor designated as r/24 is the only potentiometer that has a different resistance to compensate for the lower most branch compensating for fluid resistances 97 r, 98 r, 99 r, and 100 r.

Returning to FIG. 10, it should be noted that to effect the best separation, the sample 5 is inserted close to the cathode 23. To accomplish this, most of the flow enters through the anode buffer inlet 27 and the sample is inserted around its periphery, through an annular sample inlet 28. This carries the sample ideally near the cathode, ie. not over the center of the channel to the anode. The remaining (cathode) buffer flow is added around the periphery through a secondary buffer inlet 29. As shown in the FIG. 10, the buffer enters into an annular distribution chamber 30 and if the distribution is not sufficiently uniform, additional cathode inlets 29 to the distribution chamber are used along with an external distribution manifold (not shown) to attain the desired degree of uniformity.

The anode 22 and the cathode 23 are made of conductive materials for, but the inlet section 31 is constructed of non-conductive material to confine the electrophoresis process to the tapered annular chamber 17. Materials for the tapered anode 22 and the cathode 23 segments are corrosion resistant and are fabricated from graphite, titanium or other less corrosion resistant metals which are plated with noble metals like gold or platinum. The inlet sections 27, 28 and 29 are constructed from non-conductive material like non-conductive composites or engineering plastics.

The larger inlet tubes 27 and 29 are attached to the base 31 through the use of standard fittings, while the sample inlet 28 and the outlet lines 33 use either miniature fittings or are glued in place. The long (approximately 100 cm), small diameter outlet lines 33 meter the flow to assure approximately equal flow from the outlets 32 and provide enough pressure drop to meter the flow and clear air bubbles trapped in the tubes at startup. The outlet lines 33 also need to be long enough to reach a terminus in a manifold at a common geometric height (pressure head) for collection. These long lines effectively meter the output flow. For example, the ends of the lines could be arranged in a 10×10 horizontal array spaced so that the output flows drop into test tubes in a standard test tube rack.

The outlet ports 32 are small drilled holes in the annular segments 25 the lines 33 are inserted into larger diameter holes 33a than the outlet ports 32 which are over drilled onto the outlet ports 32. The sample inlet ports are also over drilled as well.

Non-conductive through hole bolts 34 (or conductive bolts with insulative sleeves) secure the entire package including the stack of annular electrode segments 23 with the nonconductive inlet section 31. The tapered cylindrical portion of the anode 22 is bolted into electrical contact with the cover 37 of the device with bolts 35 forming an integrated structure. Finally, it should be noted that annular ring segments 23 are provided with a generally annular recess 38. The recess 38 is of varying depth about the circumference of recess 38 decreasing in depth toward the output port 32 with the greatest depth at the output port 32 and the minimum depth at a point on the recess opposite the output port 32. The width of the recess is dependent on the ultimate size and throughput of the device and is determined as follows: The difference in the depth of the annular recess 38 is dependent upon the size of the overall structure and it is designed to equalize the pressure throughout the recess notwithstanding a removal of material at port 32. A non-conductive gasket 25 electrically separates each of the segments. The hole in the gasket is larger than the opening in the annular ring and the edge of the hole is aligned with the outer circumference of the recess 38.

Accordingly, when the device is assembled a slot 24 is formed between segments which communicates with the recess 38 and the channel 17 as shown in FIG. 10 and increases the volume in the device. In order to maximize the purity of each separated fraction of the sample, the flow out through the slot 24 must be uniform around the periphery of the chamber. This requires that the total pressure drop from the entrance of the slot to entrance of the outlet hole 32 must be the same at all points on the within periphery uniform flow. The purpose of the slot 24 which is a fraction of a millimeter thick is to provide a large flow resistance so that the variations due to flow around the periphery to the outlet is relatively small. The purpose of the larger cross section of the recess, which is about 0.25 cm$^2$, is to minimize this added pressure drop from the accumulated flow coming from opposite the outlet hole to the outlet hole. This added pressure drop tends to decrease the amount of flow from opposite the outlet decreasing the degree of uniformity. Compensation for this effect is possible by decreasing the radial length of the slot 24 with increase in the angle away from the outlet hole 32 to opposite the outlet tube. If this increase is linear with angle, the radius to the outside of the slot varies in accordance with the following formula:

$$r = r_0 + (l_0 - l_{180})\frac{\theta}{\pi}$$

Where $l_0$=length of the slot at the point on the recess at output port $l_{180}$=length of the slot at the point of the recess directly opposite the output port $\theta$=the angle between the radius at a point aligned with the output port and the radius at any point along the recess between 0° and 180°.

Figure 15:
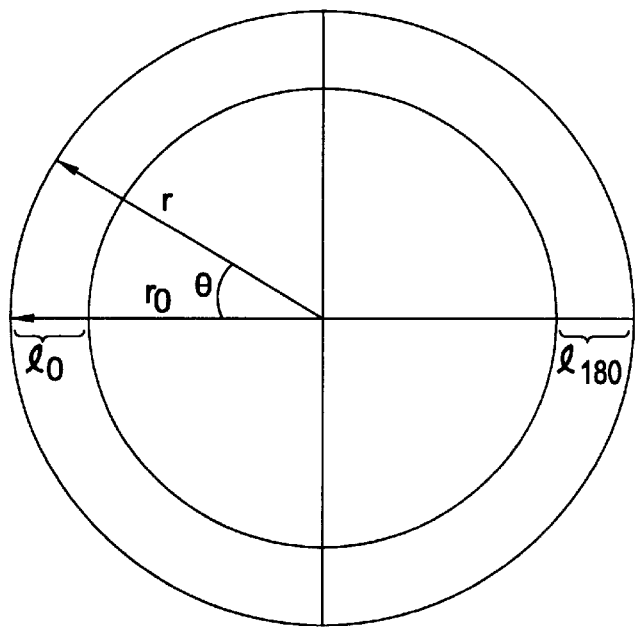
FIG. 15 shows the implementation of the formula $$r = r_0 + (l_0 - l_{180}) \frac{\theta}{\pi}$$

FIG. 15 shows the implementation of the above formula. When $l_0$ and $l_{180}$ are equal the centerline for the recess forms a circle as shown. As $l_0$ becomes greater than $l_{180}$ the length of r increases in a spiral fashion which moves the center of the radius of the recess toward the output port.

FIG. 16 illustrates the pressure equalization where the change in pressure due to the slot is equalized by the change in the pressure of the recess thereby equalizing the pressure throughout the chamber 17.

The purpose of the Annular recess in the cathode electrode segments is to equalize the flow around the periphery of the segment. For the flow to travel from opposite the outlet tube to the outlet tube, the pressure must decrease as the flow approaches the tube. Therefore, it would be desirable if the pressure drop of the slot between the segments was greater near the outlet tube to make up for this difference. For a slot of constant width this infers that the length 1 of the slot in the radial direction should be greater near the outlet. For annular recess, this can be accomplished by offsetting the center of the annular recess toward the outlet. The length of this slot can be described as one constant minus another times the cosine of the angle away from the outlet. Assuming constant flow the pressure drop of such a slot can be described as a constant, $C_1$, plus a constant, $C_2$ times the—Cosine of the Angle away from the outlet, as shown in FIG. 15.

This variation can be used to provide the decrease in pressure required for flow toward the outlet tube. What is desired is that when we add the pressure drop of the recess to that of the slot, the total pressure drop is constant as shown in FIG. 16.

Where in FIG. 16

$\Delta P_s$ change in slot pressure $\Delta P_r$ change in recess pressure

As shown in FIG. 16, the configuration of the recess should be such that the pressure decreases with a constant gradient as the uniform flow from the slot is added going around the periphery toward the outlet. Considering the pressure gradient for the recess, Darcy's pressure drop formula for linear flow can be reduced to:

$$\frac{\Delta P}{l} \sim \frac{V_{ave}}{D_H^2}$$

where $$\frac{\Delta P}{l} = \text{pressure gradient}$$

$V_{ave}$=average velocity
$D_H$=hydraulic diameter
and $$D_H = \frac{4A}{P}$$

where
A=cross sectional area or width×depth=wd
P=wetted perimeter or 2× (w+d)
Therefore, since volumetric flow G is A $V_{ave}$, it follows that:

$$\frac{\Delta P}{l} \sim \frac{GP^2}{A^3}$$

And if for the constant $\Delta P/1$ we substitute $$\left[\frac{GP^2}{A^3}\right]_{outlet}$$

we get the equality:

$$\left[\frac{GP^2}{A^3}\right]_{outlet} = \frac{4(G(w+d))^2}{d^3 w^3}$$

Now for constant width and the volumetric flow G at any angular location we can solve the following cubic polynomial for the depth of the recess, d using standard methods.

$$\left[\frac{GP^2}{A^3}\right]_{outlet} w^3 d^3 - 4Gd^2 - 8Gwd - 4Gw^2 = 0$$

Therefore, a recess can be configured that fits within the available spaces and has the desired constant pressure gradient for uniform addition of flow. Furthermore, it should be apparent to persons skilled in the art, that by applying the principles of this invention, and using other techniques, other combinations of recess and slot geometries can be made to satisfy the constant total pressure drop requirement.

Figure 11:
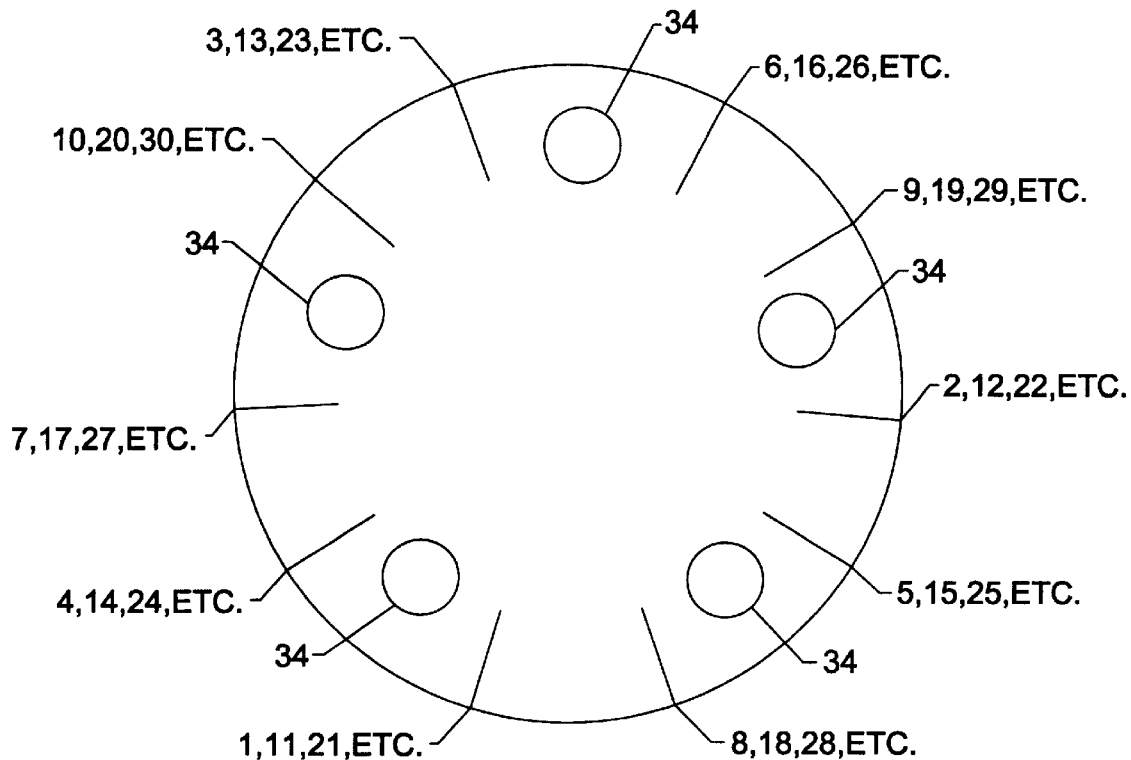
FIG. 11 shows the distribution of outlets around the periphery of the annular stack elements to maximize uniformity of flow.

While FIG. 10 shows all of the outlet ports on one side, in reality the various annular segments 24 as shown in FIG. 9 are disposed about the periphery of the electrophoresis apparatus. This permits the distribution of such outlet ports 25 around the periphery of the annular segments and position as shown in FIG. 11 and is determined by the formula i+10 n (where n=0 to 9). Thus, referring to figure for the stack of segments shown in FIG. 9 where the bottom most segment is Segment No. 1 the outlet tube (1) would be generally disposed on the left as shown. Segment No. 2, the output port (2) would be disposed as shown. In Segment No. 3, the output port cannot be seen in this view, and Segment No. 4, the output port (4) would be as shown. Segment No. 5, the output port (5) would be as shown. For Segment No. 6, cannot be seen in this figure. For the upper most segment in the figure, Segment No. 7, the port (7) would be as shown. To simplify the drawing the segment output ports shown for distribution have been illustrated with their segment position numbers in parentheses. To avoid confusion with other reference numerals the stack of the instant invention of this embodiment is 100 sections high.

While a device of specific dimensions has been described, it should be noted that a larger dimension device may be constructed to increase the throughput of the electrophoresis process where production quantities are required and other equivalent structures will be apparent to those skilled in the art.

Having thus described the invention what is claimed is:

1. A continuous flow electrophoresis apparatus for separating items of interest in a sample comprising:
   a. a chamber,
   b. at least one buffer inlet communicating with said chamber for introduction of a buffer having a generally longitudinal flow,
   c. at least one cross flow buffer inlet disposed within an input wall section of said chamber for introduction of a cross buffer flow,
   d. a source of electrical potential for applying an electrical field to said chamber that is generally transverse the longitudinal buffer flow and opposite the cross buffer flow,
   e. at least one sample inlet communicating with said chamber for introduction of said sample,
   f. a plurality of output ports disposed in an output wall section of said chamber generally opposite said input wall section for outputting buffer and the separated items of interest, and
   g. a collection device communicating with said output ports for collecting said separated items of interest at each output port.

2. A continuous flow electrophoresis apparatus as described in claim 1 wherein there are a plurality of buffer inlets.

3. A continuous flow electrophoresis apparatus as described in claim 1 further comprising:
   h. a plenum having a metering port which communicates with said chamber and an output port larger than said metering port adapted for receiving an output tube which communicates with said collection device.

4. A continuous flow electrophoresis apparatus as described in claim 1 wherein said chamber is a cylindrical chamber.

5. A continuous flow electrophoresis apparatus as described in claim 1 wherein said input wall section is positively charged and said output wall section is negatively charged.

6. A continuous flow electrophoresis apparatus for separating items of interest comprising:
   a. a linearly disposed chamber having an output side wall and an input side wall opposite said output side wall,
   b. at least one buffer inlet disposed within said input side wall of said chamber for introduction of a cross flow buffer,
   c. a source of electrical potential for applying an electrical field generally transverse of a longitudinal buffer flow and opposite said cross buffer flow,
   d. at least one sample inlet communicating with said chamber for introduction of said sample,
   e. a plurality of output ports disposed in an said output side wall of said chamber and opposite said input side wall for outputting buffer and the separated items of interest, and
   f. a collection device communicating with said output ports for collecting said separated items of interest at each output port.

7. A continuous flow electrophoresis apparatus as described in claim 6 wherein there are a plurality of buffer inlets.

8. A continuous flow electrophoresis apparatus as described in claim 6 further comprising:
   g. a plenum having a metering port which communicates with said chamber and an output port larger than said metering port adapted for receiving an output tube which communicates with said collection device.

9. A continuous flow electrophoresis apparatus as described in claim 6 wherein said input side wall is positively charged and said output side wall is negatively charged.

10. A continuous flow electrophoresis apparatus for separating items of interest comprising:
    a. a chamber,
    b. at least one buffer inlet disposed within an input wall section of said chamber for introduction of a cross flow buffer,
    c. a source of electrical potential for applying an electrical field generally transverse of a longitudinal buffer flow and opposite said cross buffer flow,
    d. at least one sample inlet communicating with said chamber for introduction of said sample,
    e. a plurality of output ports disposed in an output wall section of said chamber and opposite said input wall section for outputting buffer and the separated items of interest, said output ports separated electrically by a series of resistance elements, and
    f. a collection device communicating with said output ports for collecting said separated items of interest at each output port.

11. A continuous flow electrophoresis apparatus as described in claim 10 wherein said series of resistance elements is adjustable.

12. A continuous flow electrophoresis apparatus as described in claim 10 wherein said chamber is a linearly disposed chamber, said input wall section comprises an input side wall and said output wall section comprises an output wall section.

13. A continuous flow electrophoresis apparatus as described in claim 10 wherein said chamber is a cylindrical chamber.

14. A continuous flow electrophoresis apparatus as described in claim 10 wherein there are a plurality of buffer inlets.

15. A continuous flow electrophoresis apparatus as described in claim 10 further comprising:
    g. a plenum having a metering port which communicates with said chamber and an output port larger than said metering port adapted for receiving an output tube which communicates with said collection device.

16. A continuous flow electrophoresis apparatus as described in claim 10 wherein said input wall section is positively charged and said output wall section is negatively charged.

17. A continuous flow electrophoresis apparatus as described in claim 10 wherein said chamber tapers to an apex in a longitudinal direction.

18. A continuous flow electrophoresis apparatus for separating items of interest comprising:
    a. a chamber, said chamber tapering to an apex in a longitudinal direction,
    b. at least one buffer inlet communicating with said chamber for introduction of a buffer that flows through the chamber, c. at least one sample inlet communicating with said chamber for introduction of said sample, d. a plurality of output ports disposed in said chamber for outputting buffer and the separated items of interest, e. a source of electrical potential for applying an electrical field generally transverse of the buffer flow and opposite the flow of the buffer and the separated items of interest into said output ports, and f. a collection device communicating with said output ports for collecting said separated items of interest at each output port.

19. A continuous flow electrophoresis apparatus as described in claim 18 wherein said chamber is a linearly disposed chamber.

20. A continuous flow electrophoresis apparatus as described in claim 18 wherein said chamber is a cylindrical chamber.

21. A continuous flow electrophoresis apparatus as described in claim 18 wherein said chamber further comprises a negatively charged wall section and a positively charged wall section opposite the negatively charged wall section and said output ports are disposed in said negatively charged wall section.

22. A continuous flow electrophoresis apparatus for separating items of interest in a sample comprising:

a. a cylindrical chamber, b. a plurality of stacked buffer inlets communicating with said chamber for introduction of a cross flow buffer, said stacked buffer inlets forming a central anode, c. a source of electrical potential for applying an electrical field generally transverse a longitudinal buffer flow and opposite said cross buffer flow, d. an input section of said chamber within said central anode and comprising at least one inlet for introduction of said sample, e. an output section of said chamber formed from a plurality of annular concentric rings disposed around said central anode and defining a cathode, said output section comprising a plurality of output ports for outputting separated items of interest, and f. a collection device for collecting said separated items of interest at each output port.

23. A continuous flow electrophoresis apparatus as described in claim 22, wherein said plurality of concentric rings of said cathode are separated by a series of resistance elements.

24. A continuous flow electrophoresis apparatus as described in claim 23 wherein said series of resistance elements is adjustable.

25. A continuous flow electrophoresis apparatus as described in claim 23 further comprising:

g. a series of plenums each having a metering port which communicates with said chamber and a second port larger than said metering port adapted for receiving a tube which permits input and output through said plenums.

* * * * *

UNITED STATES PATENT AND TRADEMARK OFFICE
CERTIFICATE OF CORRECTION

PATENT NO. : 5,972,190
DATED : October 26, 1999
INVENTOR(S) : Richman It is certified that error appears in the above-identified patent and that said Letters Patent is hereby corrected as shown below:

Column 4, line 36, "alot" should read --slot--.

Column 6, line 43, "d y$^2$" should read --dy$^2$--.

Column 8, line 60, "≅" should read --=--.

Column 11, line 65, "D$^2_H$" should read --D$_H^2$--.

Column 12, line 31, "4(G(w+d))$^2$" should read --4G(w+d)$^2$--.

Signed and Sealed this

Twenty-seventh Day of March, 2001

Attest:

NICHOLAS P. GODICI

Attesting Officer

Acting Director of the United States Patent and Trademark Office